US011672515B2

(12) United States Patent
Sarna et al.

(10) Patent No.: US 11,672,515 B2
(45) Date of Patent: Jun. 13, 2023

(54) CELL COLLECTION AND PREPARATION DEVICES AND METHODS

(71) Applicant: BOSTON SCIENTIFIC SCIMED, INC., Maple Grove, MN (US)

(72) Inventors: Surbhi Sarna, San Francisco, CA (US); David Snow, San Carlos, CA (US); Christina Christman-Skieller, San Bruno, CA (US); Jesus Magana, Redwood City, CA (US)

(73) Assignee: BOSTON SCIENTIFIE SCIMED, INC., Maple Grove, MN (US)

( * ) Notice: Subject to any disclaimer, the term of this patent is extended or adjusted under 35 U.S.C. 154(b) by 312 days.

(21) Appl. No.: 16/172,165

(22) Filed: Oct. 26, 2018

(65) Prior Publication Data

US 2019/0125318 A1    May 2, 2019

Related U.S. Application Data

(60) Provisional application No. 62/578,127, filed on Oct. 27, 2017, provisional application No. 62/608,027, filed on Dec. 20, 2017.

(51) Int. Cl.
*A61B 10/02* (2006.01)
*A61M 25/10* (2013.01)
*A61B 10/04* (2006.01)

(52) U.S. Cl.
CPC .......... *A61B 10/0291* (2013.01); *A61B 10/02* (2013.01); *A61B 10/04* (2013.01);
(Continued)

(58) Field of Classification Search
None
See application file for complete search history.

(56) References Cited

U.S. PATENT DOCUMENTS

| 3,168,092 A | 2/1965 | Silverman |
| 3,664,328 A | 5/1972 | Moyle et al. |

(Continued)

FOREIGN PATENT DOCUMENTS

| DE | 3331813 A1 | 3/1985 |
| WO | 2009142605 A1 | 11/2009 |

OTHER PUBLICATIONS

Author unknown, "Cell Culture Basics", Invitrogen Handbook, [online] (date unknown) retrieved on May 6, 2019]. Retrieved from Internet URL: https://www.vanderbilt.edu/viibre/CellCultureBasicsEU.pdf, 62 pages.

(Continued)

*Primary Examiner* — Benjamin S Melhus
(74) *Attorney, Agent, or Firm* — Seager, Tufte & Wickhem, LLP

(57) ABSTRACT

According to exemplary embodiments of the present disclosure, a system for collection and analysis of cells from a body lumen of a patient may include a diagnostics device including a tube having a distal end and a proximal end and a balloon having a first end coupled to the distal end of the tube. The balloon may be disposed in the tube in a first, inverted position and movable to a second, everted position. A push wire may have a distal end coupled to a second end of the balloon. The balloon may be movable from the first inverted position to the second everted position by actuation of the push wire. One or more receptacles may be included for processing a balloon sample. The system may further include at least one of a sample preparation fluid, a sample preservation liquid, or both. The sample may be preparable for cytological analysis.

20 Claims, 8 Drawing Sheets

(52) U.S. Cl.
CPC ... *A61M 25/1002* (2013.01); *A61M 2025/105* (2013.01); *A61M 2025/1093* (2013.01)

(56) References Cited

U.S. PATENT DOCUMENTS

| | | | |
|---|---|---|---|
| 4,324,262 A | | 4/1982 | Hall |
| 4,467,816 A | | 8/1984 | Schlueter et al. |
| 4,863,440 A | | 9/1989 | Chin |
| 5,163,927 A | | 11/1992 | Woker et al. |
| 5,171,305 A | | 12/1992 | Schickling et al. |
| 5,191,899 A | * | 3/1993 | Strickland .......... A61B 10/0291 600/569 |
| 5,374,247 A | | 12/1994 | Lowery et al. |
| 5,422,273 A | * | 6/1995 | Garrison ............ A61B 10/0291 422/547 |
| 5,472,419 A | * | 12/1995 | Bacich .............. A61M 25/0068 604/515 |
| 5,524,634 A | * | 6/1996 | Turkel .............. A61B 10/0096 600/562 |
| 5,738,109 A | | 4/1998 | Parasher |
| 6,383,805 B1 | | 5/2002 | Latimer |
| 6,514,224 B1 | * | 2/2003 | Anapliotis ............ A61B 10/00 206/209 |
| 6,840,946 B2 | | 1/2005 | Fogarty et al. |
| 7,255,687 B2 | | 8/2007 | Huang et al. |
| 8,152,739 B1 | * | 4/2012 | McCully ............ A61B 10/0291 600/569 |
| 8,470,043 B2 | | 6/2013 | Schaller et al. |
| 8,652,067 B2 | | 2/2014 | Lonky et al. |
| 9,028,401 B1 | | 5/2015 | Bacich et al. |
| 9,161,773 B2 | | 10/2015 | Schaller et al. |
| 9,282,951 B2 | | 3/2016 | Lonky et al. |
| 9,320,502 B2 | | 4/2016 | O'Sullivan et al. |
| 9,492,570 B2 | | 11/2016 | Sirimanne et al. |
| 9,493,839 B2 | | 11/2016 | Speiser et al. |
| 2003/0208223 A1 | | 11/2003 | Kleiner |
| 2004/0030263 A1 | | 2/2004 | Dubrul et al. |
| 2005/0021069 A1 | | 1/2005 | Feuer et al. |
| 2006/0079924 A1 | | 4/2006 | Sanders et al. |
| 2010/0092962 A1 | | 4/2010 | Loktionov et al. |
| 2012/0259401 A1 | | 10/2012 | Gerrans et al. |
| 2012/0315662 A1 | | 12/2012 | Linnemeier |
| 2013/0137094 A1 | * | 5/2013 | Espina ..................... G01N 1/30 435/6.11 |
| 2013/0267870 A1 | | 10/2013 | Lonky |
| 2013/0338533 A1 | | 12/2013 | Olsen |
| 2014/0128732 A1 | | 5/2014 | Roy et al. |
| 2014/0257098 A1 | | 9/2014 | Del Priore |
| 2015/0057565 A1 | | 2/2015 | Mazzoli, Jr. et al. |
| 2016/0074022 A1 | * | 3/2016 | Oliva ................. A61B 10/0291 600/569 |
| 2016/0278747 A1 | * | 9/2016 | Chin ................. A61B 10/0291 |
| 2017/0354437 A1 | | 12/2017 | Bacich |
| 2018/0014773 A1 | | 1/2018 | Barton et al. |

OTHER PUBLICATIONS

Fitzgerald, M. G., and Hosking, C. S., "Cell structure and percent viability by a slide centrifuge technique," Journal of Clinical Pathology, 35(2):191-194 (1982).

Miki, Y., et al. "A Strong Candidate For The Breast And Ovarian Cancer Susceptibility Gene BRCA1", Science 226 (5182):66-71 (1994).

Burke, W., "Genetic Testing" N Engl J Med 2002; 347:1867-1875.

Matsui, S., et al., "Developing And Validating Continuous Genomic Signatures In Randomized Clinical Trials For Predictive Medicine" [online] (2012) [retrieved on May 6, 2019]. Retrieved from Internet URL: http://clincancerres.aacrjournals.org/content/early/2012/10/12/1078-0432.CCR-12-1206.full-text.pdf, 7 pages.

Ellisen, L., et al., "Tumor Genotyping Brings Personalized Targeted Therapies To Patients" Advances at the Mass General Cancer Center, 6-8 (2010).

Mostertz, W., et al., "Age- And Sex- Specific Genomic Profiles In Non-Small Cell Lung Cancer" JAMA 303(6): 535-543 (2010).

Lee, Y., et al., "A Candidate Precursor To Serous Carcinoma That Originates In The Distal Fallopian Tube" Journal of Pathology 2007, 211:26-35 (2006).

International Search Report and Written Opinion for application PCT/US2018/057765, dated Mar. 1, 2019, 12 pages.

C. Crum, "Intercepting Pelvic Cancer In The Distal Fallopian Tube: Theories And Realities" Molecular Oncology 3, 165-170 (2009).

\* cited by examiner

CELL COLLECTION AND PREPARATION DEVICES AND METHODS

CROSS-REFERENCE TO RELATED APPLICATIONS

This application is a nonprovisional application of, and claims the benefit of priority to, U.S. Provisional Application Ser. No. 62/578,127, filed Oct. 27, 2017, entitled "Process for Cell Collection and Preparation," and U.S. Provisional Application Ser. No. 62/608,027, filed Dec. 20, 2017, entitled "Process for Cell Collection and Preparation," the entire disclosures of which applications are expressly incorporated by reference herein.

FIELD

The present disclosure generally relates to systems and processes for collecting and preparing cells of a patient, and in particular to systems and processes for collecting and preparing cells from a body lumen, which may include a Fallopian tube.

BACKGROUND

As an example, ovarian cancer is a significant disease in women, in which 1 out of 72 women in the United States may be diagnosed with this illness during her lifetime. In 2012, over 22,000 women in the United States were diagnosed with ovarian cancer. Early detection of ovarian cancer may be difficult due to a lack of effective screening tests, such that ovarian cancer may not be diagnosed until the disease has reached advanced stages, limiting treatment options.

Screening for ovarian cancer may typically include a surgical procedure for obtaining cell samples for diagnosis. For example, because the ovaries are intra-abdominal, laparoscopic or open surgery (laparotomy) may be performed to access the ovaries. Any surgical procedure increases a risk to the patient, including but not limited to experiencing an adverse reaction, and/or requiring significant recovery time. Additionally, an ovary biopsy may expose the patient to additional risk of potentially spreading diseased (e.g., cancerous) cells.

Underlying biological differences in ovarian malignancy gene expression among patients with different clinicopathologic characteristics may be difficult to determine. A deeper understanding of molecular abnormalities at a pathway level may be beneficial to understanding the complex mechanisms of ovarian cancer oncogenesis, shed light on the biological underpinnings contributing to survival differences, and/or further help identify specific cohorts of patients that may be more receptive to individualized therapeutic strategies. Thus, in the exemplary case of ovarian cancer and with other conditions, there exists a need for a less invasive process to allow cell samples to be obtained from a Fallopian tube and other fragile, anatomically difficult to navigate body lumens, without damaging such lumens, for evaluation of cancer and other malignancies or abnormalities. There further exists a need for securing samples of representative cells from the Fallopian tube and other body lumens to screen for early stage cancers and to further analyze when a cancer is determined to be present.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a system for collection and analysis of cells from a body lumen of a patient may include a diagnostics device including a tube having a distal end and a proximal end and a balloon having a first end coupled to the distal end of the tube. The balloon may be disposed in the tube in a first, inverted position and movable to a second, everted position. A push wire may have a distal end coupled to a second end of the balloon. The balloon may be movable from the first inverted position to the second everted position by actuation of the push wire. The system may further include one or more receptacles for processing a balloon sample, and at least one of a sample preparation fluid, a sample preservation liquid, or both. The balloon sample may be preparable for cytological analysis In various of the foregoing and other embodiments of the present disclosure, in the second, everted position a surface of the balloon may be contactable with an inner surface of the body lumen to collect a plurality of cells. The balloon and the collected cells may be separable from the diagnostics device for the processing of the balloon sample. The diagnostics device may further include a sheath coaxial with the tube and slidably adjustable relative to the tube to cover at least a first length of the balloon extending outward from the distal end of the tube in the second, everted position. The diagnostics device may further include a filament extendable distally of the first end of the balloon. The balloon, the sheath, or the filament, or combinations thereof, may be separable into the one or more receptacles for processing the balloon sample, a sheath sample, or a filament sample, or combinations thereof, for cytological analysis of the collected cells. The balloon sample, the sheath sample, or the filament, or combinations thereof, may include spinning the one or more receptacles in a centrifuge. The system may further include evaluating the balloon sample, the sheath sample, or the filament, or combinations thereof for malignancies, or abnormalities, or both. The system may further include retaining cells from the balloon sample, the sheath sample, or the filament, or combinations thereof under conditions suitable for genetic testing of the cells. They system may further include a compiled cell library. The cytological analysis of the collected cells may be analyzable against the compiled cell library. The cytological analysis of the collected cells may be performable for a plurality of patients and may be compilable into the cell library. The cells from the plurality of patients may be sequenceable such that genetic code information from the sequenced cells for each of the plurality of patients may be determinable, wherein the genetic code information may be compilable for the plurality of patients into a genetic code library. A treatment, a clinical outcome, or both, of a selected patient from the plurality of patients may be determinable with the collected cells from the selected patient and the cell library. The collected cells from the plurality of patients may form an array.

According to an exemplary embodiment of the present disclosure, a method of collecting and preparing cells from a body lumen in a patient may include everting a balloon into the body lumen and collecting cells from the body lumen on an outer surface of the balloon when the balloon is everted. Collected cells from the patient on the balloon may be removed. At least a first portion of the balloon may be separated. A first cell sample from cells on the first portion of the balloon may be prepared.

In various of the foregoing and other embodiments of the present disclosure, the first portion of the balloon may be separated into a first receptacle. The body lumen may be a Fallopian tube, and the balloon may be inflatable and extendable longitudinally into the Fallopian tube during eversion. The outer surface of the balloon may be textured. At least a second portion of the balloon may be separated into a second receptacle, and a second cell sample from cells on the second portion of the balloon may be prepared. A method of treating a disease condition in a patient, may include maintaining a cell library, the cells for the cell library may include cells collected from a plurality of patients by a method of collecting and preparing cells from a body lumen in a selected patient, such as described above, including everting a balloon into the body lumen and collecting cells from the body lumen on an outer surface of the balloon when the balloon is everted. Collected cells from the patient on the balloon may be removed. At least a first portion of the balloon may be separated. A first cell sample from cells on the first portion of the balloon may be prepared. A cell sample may be received from a selected patient, and the cell sample from the selected patient may be compared with the cell library. A treatment recommendation may be provided based on the comparison. The cell library may include information regarding treatments and clinical outcomes of the plurality of patients correlated with cells of the cell library. A diagnostics device, as part of a system for collection and analysis of cells from a body lumen of a patient, as part of a method of collecting and preparing cells from a body lumen of a patient, and/or as part of a method of treating a disease condition including collecting cells from a plurality of patients for a cell library and/or from a selected patient for comparing with the cell library, may further include any of: a tube having a distal end and a proximal end and a balloon having a first end coupled to the distal end of the tube; the balloon may be disposed in the tube in a first, inverted position and movable to a second, everted position; a push wire may have a distal end coupled to a second end of the balloon; the balloon may be movable from the first inverted position to the second everted position by actuation of the push wire; a system may include one or more receptacles for processing a balloon sample, and at least one of a sample preparation fluid, a sample preservation liquid, or both. A sheath may be coaxial with the tube and slidably adjustable relative to the tube to cover at least a first length of the balloon extending outward from the distal end of the tube in the second, everted position; and a filament may be extendable distally of the first end of the balloon. The balloon, the sheath, or the filament, or combinations thereof, may be separable into the one or more receptacles for processing the balloon sample, a sheath sample, or a filament sample, or combinations thereof, for cytological analysis of the collected cells.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
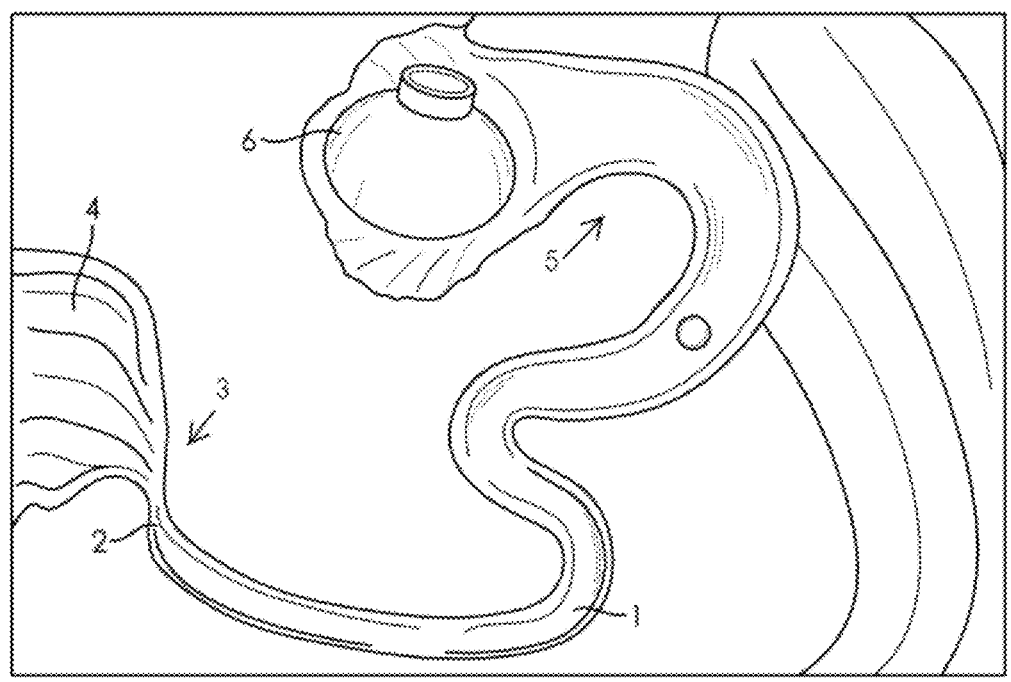
FIG. 1 illustrates a cross-sectional view of a Fallopian tube with the uterotubal junction (UTJ) that connects the uterus to the ovaries.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As described above, a challenge in understanding ovarian cancer may be in the retrieved samples from patients. Researchers have had difficulties finding precursor lesions to ovarian cancer, particularly the most common, the most aggressive and the most lethal subtype called high grade serous carcinoma within ovaries. In the past, researchers started reporting discovery of dysplastic or neoplastic lesions in the epithelium of the distal or the fimbriated end of Fallopian tubes, but not in the ovaries removed from BReast CAncer susceptibility gene (BRCA) mutation carriers undergoing prophylactic bilateral salpingo-oophorectomy (BSO). When subject to immune-histochemical staining, these precursor lesions called serous tubal intraepithelial carcinoma (STIC) showed p53 accumulation, a hallmark of serous carcinoma. Additional studies involving genetic mutational analyses of metastasized ovarian tumors found that the same unique TP53 mutation was often found in both the ovarian cancer cells and pre-cancerous cells in Fallopian tubes, demonstrating that indeed the Fallopian tube was often the site of origin.

With numerous studies supporting these findings, it has now been widely accepted among the oncology and the gynecology communities that in the vast majority of cases, high-grade serous carcinoma may originate in the Fallopian tubes and subsequently spread to ovaries through contact and exchange of cells between the ovaries and the fimbriated end Fallopian tubes. With this understanding, the ability to safely test cells in the Fallopian tube for malignancy may be beneficial for the early detection and treatment of such cancers.

The introduction of diagnostic devices into a delicate body lumen (e.g., Fallopian tube) presents challenges since the body lumen may be difficult to navigate and may be prone to perforation during passage of most devices. For example, with respect to the Fallopian tube, perforation may occur at the uterotubal junction (UTJ), a constriction that occurs approximately 1 cm distal to the proximal os (opening) of the Fallopian tube in the uterus. The lumen size at this constriction may be as small as approximately 0.3 mm to 0.5 mm, while the lumen size of the Fallopian tube adjacent to the uterotubal junction may be approximately 1 mm. Referring now to FIG. 1, a Fallopian tube 1 of a patient may extend from a proximal os 3 to a uterus, connecting at a uterotubal junction (UTJ) 2, to a distal os 5 and connecting to ovaries 6. A perforation may occur at the UTJ 2, which is a constriction occurring distal to the proximal os 3 (e.g., opening) of the Fallopian tube. For example, in some patients the UTJ 2 may be approximately 1 cm distal of the proximal os 3.

Although the description refers to sample collection and analysis of cells retrieved from Fallopian tubes, it is understood that systems and methods of sample collection and analysis may be applicable to any other body lumens, tubes, and ducts, including but not limited to a bile duct, hepatic duct, cystic duct, pancreatic duct, lymphatic vessels, lacrimal ducts, blood vessels, and circulatory vessels, and vasculature, in accordance with the present disclosure. For example, in addition to collecting and analyzing potentially cancerous or other abnormal cells, cells may be collected for analyzing a level of plaque build-up, and/or endothelial cells.

Exemplary embodiments in accordance with the present disclosure may collect and prepare cells from the interior wall of the Fallopian tube or other fragile, anatomically difficult to navigate body lumens for diagnostic purposes and analysis. A process is provided for collecting such cells in a less invasive procedure and preparing such cells for cytology, histology, genetic testing and sequencing, and/or cell culturing.

Various embodiments of the present disclosure may provide a process of collecting and preparing cells from a lumen in a subject. The subject may be a human patient or an animal patient. The lumen of the patient may be any lumen within the body of the patient, e.g., a body lumen. Embodiments of the present disclosure may be suited for cell collection from fragile lumens found throughout the body of a patient, for example, those found in the brain, vascular system, the lymphatic system, lacrimal ducts, and/or the Fallopian tube. As described above, FIG. 1 illustrates a Fallopian tube 1 with the uterotubal junction (UTJ) 2 that connects the uterus 4 to the ovaries 6, and illustrates an environment in which embodiments of the present disclosure may be implemented and is not intended to limit the scope of this disclosure. The process may be carried out by a physician, a veterinarian, or any other suitable clinician.

FIGS. 2A, 2B, 3, 4, 5A, and 5B illustrate exemplary embodiments of a diagnostic device that may be used to carry out a process according to exemplary embodiments of the present disclosure. It is understood that features shown and described with respect to FIGS. 2A, 2B, 3, 4, 5A, and 5B may be combined together to form exemplary embodiments of the present disclosure. These examples are not intended to limit the scope of the present disclosure.

Figure 2A:
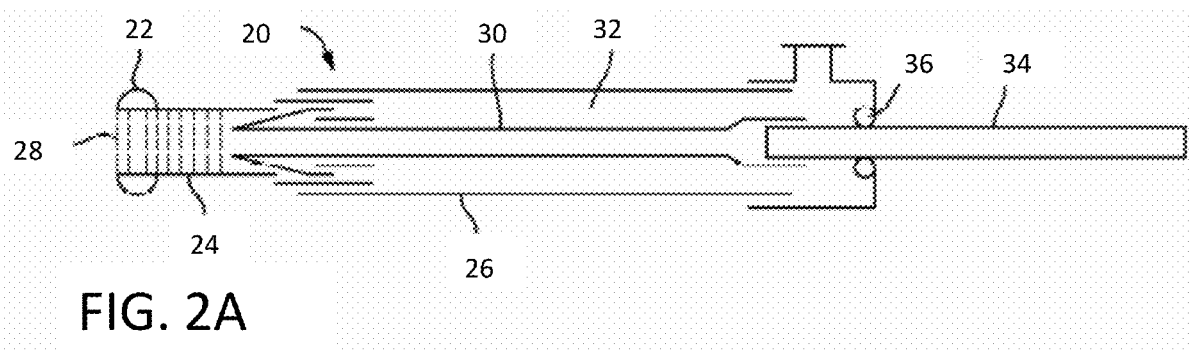
FIG. 2A illustrates a cross-sectional side view of an exemplary embodiment of a ball tip everting balloon catheter prior to deployment of the balloon in accordance with the present disclosure.
Figure 2B:
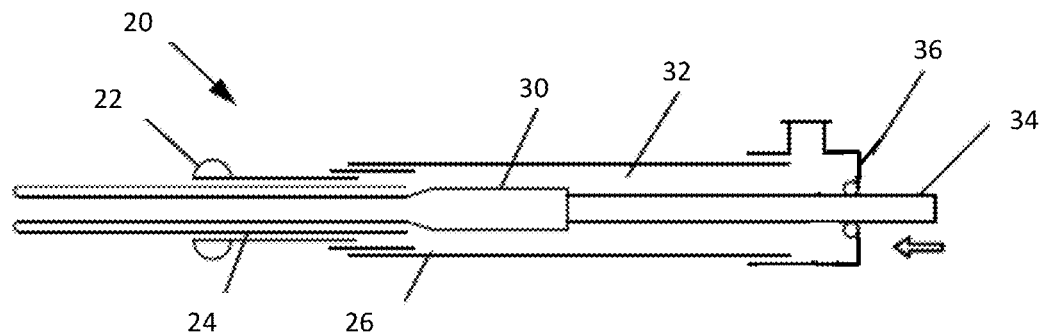
FIG. 2B illustrates a cross-sectional side view of an exemplary embodiment of the ball tip everting balloon catheter of FIG. 2A in a deployed state in accordance with the present disclosure.

Referring now to FIGS. 2A-2B, in some embodiments, a ball tip everting balloon catheter 20 may be used for carrying out an exemplary embodiment of a process in accordance with the present disclosure. The catheter 20 may include an introduction catheter or tube 26, an everting balloon 30, and a push rod, or push wire 34. It is understood that "tube" and "catheter" 26 may be used interchangeably. The catheter 26 may be a sheath for protecting and/or delivering the balloon 30 into the target body lumen (e.g., Fallopian tube). In some embodiments, the catheter 26 may be a generally flexible tube or a generally rigid tube, e.g., a cannula. In some embodiments, the balloon 30 may extend inside a main lumen 32 of the catheter 26 in an inverted position, and a proximal end of the balloon 30 may be attached to the push wire 34. The push wire 34 may be movable relative to the catheter 26, e.g., by passing through a proximal end of the catheter 26. In use, the catheter 26 may be advanceable to a junction of a target lumen, where the push wire 34 is then advanced through the proximal end of the catheter 26. Advancement of the push wire 34 may cause a controlled eversion of the balloon 30 out of the catheter 26, through the length of the patient's body lumen (e.g., Fallopian tube).

FIGS. 2A and 2B illustrate cross-sectional views of an exemplary embodiment of a ball tip everting balloon catheter 20 in accordance with the present disclosure, and is also described in U.S. patent application Ser. No. 14/764,710, filed Jul. 30, 2015, entitled "Methods and Devices for Fallopian Tube Diagnostics," U.S. patent application Ser. No. 15/053,568, filed Feb. 25, 2016, entitled "Methods and Devices for Fallopian Tube Diagnostics," and U.S. patent application Ser. Nos. 15/998,507 and 15/998,501, filed Aug. 16, 2018, entitled "Systems, Methods, and Devices for Fallopian Tube Diagnostics," which are herein incorporated by reference in their entireties. A spherical ball 22 may be attached to the distal end of a spring tip 24 affixed to the tube or catheter 26. The spherical ball 22 may be provided to negotiate through a patient's UTJ to minimize and/or avoid inadvertent penetration through the UTJ sidewalls. The spring tip 24 may allow the distal end with the ball 22 to flex around corners and navigate through the UTJ. The spring tip 24 and spherical ball 22 have an open lumen 28 extendable through the spring tip 24 and the spherical ball 22. The spherical ball 22 on the spring tip 24 may be approximately 0.8-1.0 mm in diameter, and the hollow spring tip 24 may have a length of approximately 1.5-2 cm, and an outer diameter of approximately 0.6 mm. The hollow spring tip 24 may be formed of a metal (stainless steel or superelastic metal, e.g., Nitinol) coil spring sheathed on the outside with thin walled polymer heat shrink tubing, made of nylon, PET (polyethylene terephthalate), or similar material. In some embodiments, the spring tip 24 may be a metal coil spring co-extruded into a tubular polymer body. The hollow spring tip 24 may also be a flexible polymer tube, and in some embodiments may be made of nylon, Polyethylene terephthalate (PET), polyether block amide, or similar materials. The everting balloon 30 may lie inside the hollow spring tip 24. The everting balloon 30 may extend proximally inside the main lumen 32 of the introduction catheter 26 (e.g., a generally flexible tubular structure) or cannula (e.g., a generally rigid tubular structure).

The proximal end of the everting balloon 30 may be attached to a push wire 34 passable through a seal 36 on the proximal end of the catheter 26 or cannula. In operational use on a patient, the flexible ball tip 22 may be manually advanced through the UTJ. Once passage of the flexible ball tip 22 and spring tip 24 through the UTJ occurs, the push wire 34 may be advanced through the seal 36 of the previously pressurized introduction catheter 26 or cannula. Advancement of the push wire 34 may cause a controlled eversion of the balloon 30 out of the hollow spring tip 24, through the length of the body lumen (e.g., Fallopian tube).

In some embodiments, when the balloon that is initially inverted into a catheter lumen is deployed, the balloon may evert upon pressurization inside the catheter. The unrolling mechanism of the eversion may create a path through the body lumen (e.g., Fallopian tube) regardless of tortuosity or constriction in the body lumen. In some embodiments, the balloon may have an elastomeric linear expansion that is less than 10% and as a result may not glide past contacting cells and instead may fold, or overlap portions of the balloon surface, with less than full inflation pressure. In some embodiments, the balloon may evert by a push wire advancement, which may be in concert with pressurization. A great majority of the length of the balloon may be substantially inelastic, such that the balloon does not substantially expand and dilate the body lumen as it everts. Balloon expansion may burst or otherwise damage or injure the body lumen.

Figure 4:
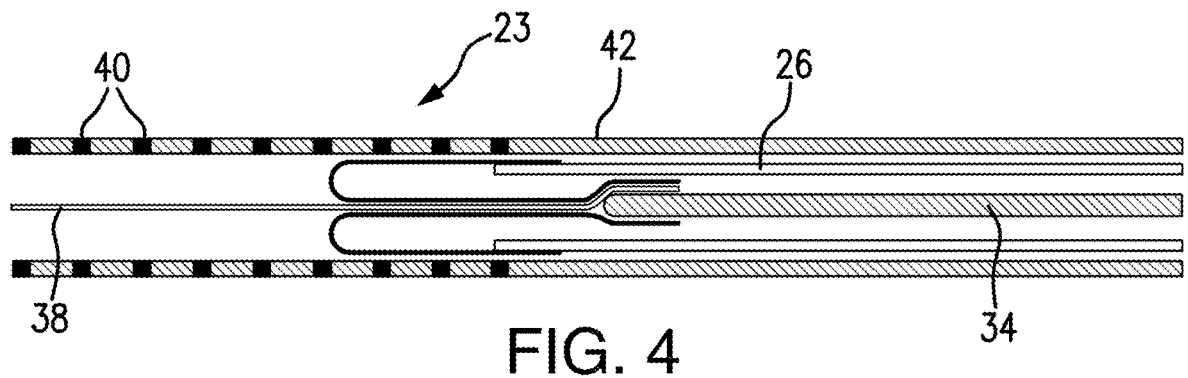
FIG. 4 illustrates a partial cross-sectional side view of an exemplary embodiment of an everting balloon catheter in a retracted state in accordance with the present disclosure.

In some embodiments, a balloon catheter 23 as shown for example, in FIG. 4, may include a filament, or suture 38 initially disposed at least partially within and extendable distally beyond the balloon 30. The filament 38 may be a string or suture, and the terms may be used throughout the present disclosure interchangeably. In some embodiments, the suture 38 may include one or more knots. Cells may be collectable by the filament or suture 38, e.g., cells may transfer from an inner surface of the body lumen (e.g., Fallopian tube) to the filament or suture 38, when the filament 38 is extended into the Fallopian tube during balloon eversion. Additionally, the length of the suture may be predetermined, and may include incremental indicia indicative of a length of extension along the filament or suture 38. Incremental indicia may measure the reach of the collection device within a Fallopian tube to aid in controlled eversion of the balloon 30. In some embodiments, cells collected on the filament or suture 38 may provide a physical correlation as to where a given cell originated within the Fallopian tube being sampled.

Figure 5A:
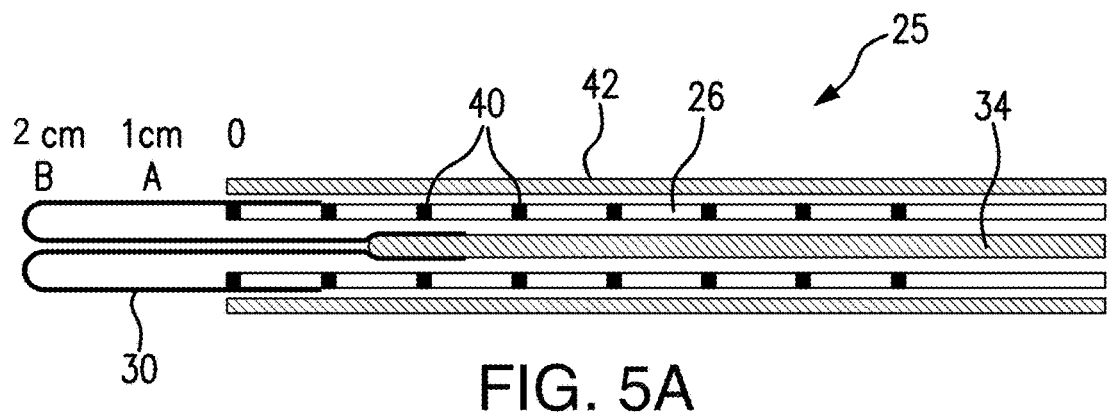
FIG. 5A illustrates a partial cross-sectional side view of an exemplary embodiment of an everting balloon catheter in a deployed state in accordance with the present disclosure.
Figure 5B:
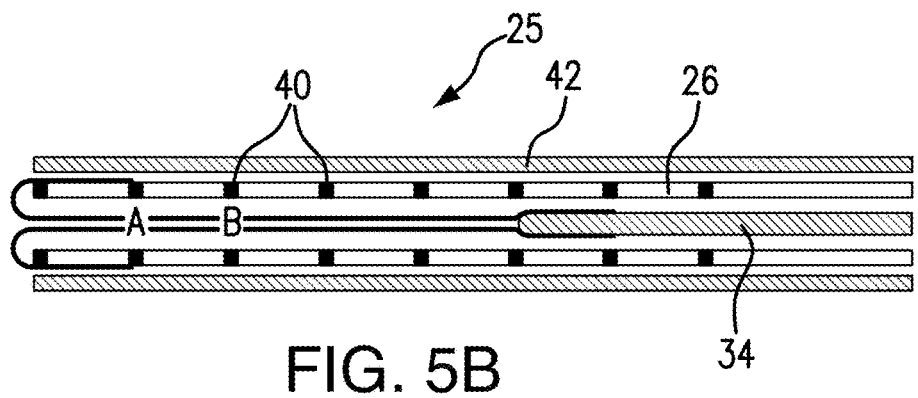
FIG. 5B illustrates a partial cross-sectional side view of an exemplary embodiment of an everting balloon catheter of FIG. 5A in an inverted position in accordance with the present disclosure.
Figure 6:
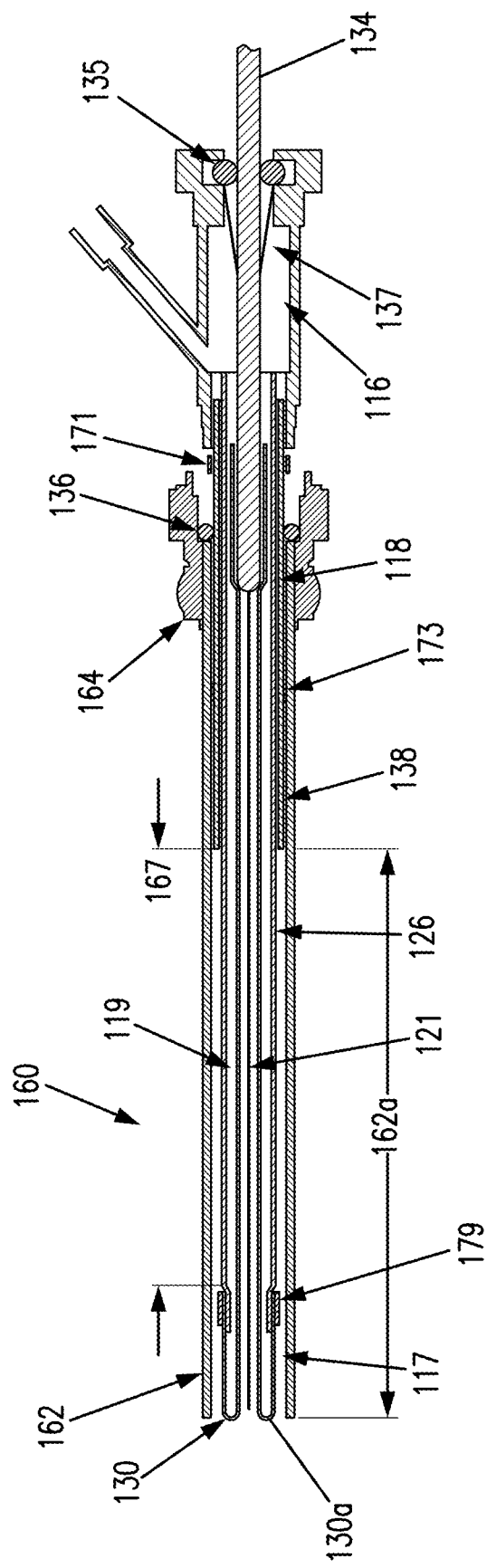
FIG. 6 illustrates a cross-sectional view of an exemplary embodiment of an everting balloon catheter in accordance with the present disclosure.

As shown in FIGS. 3, 4, 5A-5B, and 6, some embodiments of the catheter 21, 23, 25 may include a plurality of fiducial markers 40 disposed along at least a portion of the catheter 26, the balloon 30, the sheath 42, or the suture 38, or combinations thereof. FIGS. 3, 4, and 5A-5B illustrate partial views of a catheter, and it is understood that any of the features described may be included in the entire device as illustrated in FIG. 6. The markers may be formed as a score line, a coating substance, or band of material, or combinations thereof. Markers 40 may be any of radiopaque markers, radiopaque marking materials (e.g., including markers visible by way of CT scan, X-ray, or MRI scan), radio-opacity markers, isotopic markers, and/or radiofrequency markers. In some embodiments markers may be incrementally spaced apart in known predetermined distances from each other such that a medical professional may use the markers as a visual counter or measuring device to verify an approximate length of balloon, sheath, and/or suture that has been everted. In some embodiments, the catheter 26, the balloon 30, and/or the sheath 42, may at least partially be formed of a transparent material such that the markers 40 may be visible to the user. This may aid the user to verify that the balloon is everting, e.g., the device is deploying.

Referring now to FIG. 6, a cross-sectional side view of a balloon tip catheter, or device, 160 in accordance with the present disclosure is shown. In some embodiments, a balloon 130 may have an outer diameter of approximately 0.8-1.0 mm, and may have an initial everted length of approximately 1-3 cm, e.g., approximately 1.2-1.5 cm extending out of the distal end of the catheter 126 or cannula. The balloon 130 may be fully evertible into the body lumen, or Fallopian tube, e.g., extending approximately 7-12 cm. The balloon 130 may be securable to a distal end of the catheter shaft or tube 126, as indicated at reference numeral 117, and a push wire 134, as indicated at reference numeral 118. For example, the distal end 118 of the push wire 134 may form an end of the balloon 130. In embodiments, the balloon 130 may be bonded to the distal end 118 of the push wire 134. The push wire 134 may actuate the balloon 130 from an inverted position in the catheter 126 to an everted position when an interior of the balloon, between the catheter 126 and the balloon 130 and indicated by reference numeral 119, is pressurized. In embodiments, an everted position may include at least a portion of the balloon 130 extending beyond the distal end of the tube 126. In some embodiments, the balloon 130 may be initially partially everted and fixed to the catheter 126, forming a rounded end 130a. In some embodiments, the balloon 130 may be inflatable with fluid to a pressure of approximately 14-24 atm (206-353 psi).

In some embodiments, the device 160 may include a sheath 162. The sheath 162 may be coaxial with the catheter 126. The sheath 162 may be slidably adjustable relative to the catheter 126 to cover at least a first length of the balloon 130 extending outward from the distal end of the tube 126 in an everted position. The sheath 162 may form a physical barrier between the balloon 130 and the interior of the scope, through which the catheter may be inserted, to protect the balloon. For example, an initial length, e.g., approximately 1.5 cm of the balloon 130, may be extended from the catheter 126 during insertion through the scope. As the balloon is actuated (e.g., via the push wire 134 and/or balloon pressurization), the sheath 162 may protect the balloon in at least one of the inverted position, a partially everted position, or a fully everted position, or combinations thereof.

The sheath may also act to provide column strength to the balloon as it is everted. In some embodiments, a portion of the sheath 162 may be at least partially translucent, optically transparent, or combinations thereof, as indicated at reference numeral 162*a*. In embodiments, the transparent portion 162*a* of the sheath 162 may at least partially overlap with a transparent portion 167 of the catheter 126. For example, a medical professional may be able to visualize the balloon 130 (e.g., to confirm positioning and/or full balloon extension) with the hysteroscope 20 through at least a portion of the sheath 162 and/or the catheter 126. In some embodiments, the catheter may include a sheath knob 164 located at a proximal end of the sheath 162 to connect the sheath 162 to the tube 126.

The pressurized balloon 130 may have a rounded end 130*a* for atraumatic cannulation of and advancement within the body lumen (e.g., cannulation of the proximal os and advancement within the Fallopian tube) and a degree of flexibility along the balloon 130 length. The balloon 130 may have sufficient column strength to allow the balloon 130 to be manually advanced through the UTJ, for example, with a push wire 134, under at least a partial pressure or no pressure. In some embodiments, the balloon 130 may be constructed of a thin-walled polymer material, such as polyethylene terephthalate (PET), polyethylene, Nylon, polymer, or a similar material. The balloon 130 may have a wall thickness from approximately 0.0001 to 0.001 inches and in some embodiments between approximately 0.00019 and 0.00031 inches. In some embodiments, the balloon 130 may have a thickness of less than 0.005 inches. The material and/or thickness of the balloon may be important characteristics of the balloon impacting how the balloon acts as it is deployed and with respect to cell collection. For example, too thin of a balloon wall may result in the balloon lacking sufficient column strength (acting more compliant or elastic as desired), or too thick of a balloon wall may result in the balloon resisting everting or everting in an inconsistent manner. The thickness of the material may affect the contouring, wrinkling of the balloon surface to the extent the surface features are created or enhanced by the act of inverting, when loading the balloon in the catheter, which in turn may affect the ability to collect and retain cells. The material of the balloon may also impact whether the balloon may adhere or tend to stick to itself during eversion or after being deflated and withdrawn with the catheter.

In some embodiments, a first marker 171 may be disposed on at least a portion of catheter 126. The first marker 171 may be a preparation marker, indicating a desired position of the sheath knob 164. When the sheath knob is aligned with the first marker 171, the proximal end of the sheath 162 may be a reference point for the medical professional for balloon extension during preparation and initial cannulation of the balloon 130 into the body lumen (e.g., Fallopian tube). In embodiments, at least a portion of the catheter 126, e.g., a proximal portion connected to the transparent portion 167, may be formed of a metal such as stainless steel, or other materials such as composites, or polymers, or combinations thereof. The first marker 171 may indicate to a user an appropriate location of male luer lock fitting, or sheath knob, 164 with respect to the balloon 130 within the sheath 162, so that the sheath 162 may be extended distally an initial length as a preparation step to cover, for example, approximately 10 to 20 mm length of everted balloon 130 that is used to access the proximal os before the balloon is completely everted.

When in position, e.g., at the proximal os of the Fallopian tube, the sheath may be pulled back from the first marker 171 to the original position, exposing the partially everted balloon tip for accessing and placement in the body lumen. In embodiments, the sheath 162 may be extendable along a longitudinal axis to a point beyond the distal end of the catheter 126. When the sheath 162 is extended distally of the catheter 126, a distal tip of the sheath 162 may be an indicator for balloon advancement. The first marker 171 may include a score line, a coating substance, or a selectively oxidized region. In some embodiments, the first marker 171 may be an opaque band of material (e.g., including but not limited to polymer, or metal, or combinations thereof) attachable to at least a portion of the catheter 126 (e.g., metal portion, or hypotube 138) using, for example, an adhesive, bonding, or welding process. Such a preparation marker may allow the medical professional to know how far to deploy the balloon 130 in the initial preparation step, thereby improving the ease of use of the device by eliminating the need for an outside measuring tool and improving the safety of the procedure by eliminating any guesswork or eyeballing on the part of the user.

In some embodiments markers may be incrementally spaced apart in known predetermined distances from each other such that a medical professional may use the markers as a visual counter or measuring device to verify an approximate length of balloon that has been everted. It is appreciated that any inner cannula or catheter described herein may include indicia as described for assistance in navigating patient anatomy.

In some embodiments, a second marker 173 may be disposed on the catheter 126, e.g., a hypotube 138, which in some embodiments may be formed of a metal, to indicate a desired location of sheath knob 164 to confirm that the sheath 162 covers the deployed everting portion (balloon, suture, etc.) during device removal into the hysteroscope 20. For example, the second marker 173 may be a retraction marker. This may allow the user to visualize and confirm that the balloon 130 is fully protected by the sheath 162 during the removal process to avoid loss of cells collected on the balloon and/or extended portion. When the hysteroscopic view is obscured, for example, by blood or tissue in the distension fluid, additional user visualization by the second marker 173 may be advantageous. The second marker 173 may be formed by the same techniques used to form the first marker 171. The second marker 173 may also be included on any inner cannula or catheter described herein.

In some embodiments, a portion 167 of the catheter 126 and/or distal portion of sheath 162 may have a transparent section along its length or a portion that is translucent, optically transparent, or a combination thereof under use conditions. According to embodiments of the present disclosure, the tube or catheter 126 may include at least one visual marker. In other embodiments, the visual marker on the catheter 126 may comprise a third marker 179 disposed on the catheter 126. The third marker 179 may be located near or at the distal end of the catheter 126 shaft where the balloon 130 is connected to the catheter 126. In some embodiments, the third marker 179 may be radio opaque. The third marker 179 may visually indicate to a user the end of the catheter 126 shaft, thereby improving control of the catheter 126. The ability to visualize the end of the catheter 126 may be desirable during cannulation, when the balloon 130 is advanced beyond sheath 162 into the body lumen. The third marker 179 may allow a user to visualize the distal end of the catheter 126 as the cannulation step progresses. The user may be able to see when the cannulation step is complete, e.g., when the third marker 179 aligns with the end of the sheath 162 at the os, thereby improving ease of use. The third marker 179 may be formed by the same techniques used to form the first marker 171 and/or the second marker 173. The third marker 179 may be provided in an easy to see color, for example black or blue.

In some embodiments, a string, braid, and/or suture 121 may be extendable distally of the balloon 130 as the balloon 130 everts in the form of an extendable portion of the balloon 130. In some embodiments, the string or suture may be attached to the distal end of the push wire or to the balloon tip, by bonding or adhesive, e.g., at reference numeral 118. In an inverted position of the balloon 130, the string, braid, and/or suture 121 may be positioned internal to the balloon 130, e.g., within the tube of the catheter 126 as shown in FIG. 6. Upon eversion of the balloon 130, e.g., by actuation of the push wire, the string, braid, and/or suture may extend to a position that becomes the exterior to the balloon, either extending distally from the distal tip of the balloon 130, or extending proximally from the balloon tip alongside the exterior of the balloon.

The proximal end of the everting balloon 130 may be attached to a push wire 134 passable through a seal 135 on the proximal end of the catheter 126 or cannula. In operational use on a Fallopian tube of a patient, the cannula or catheter 126 may be manually advanced through the UTJ. Once passage of the cannula or catheter 126 through the UTJ occurs, the push wire 134 may be advanced through the seal 135 of the previously pressurized introduction catheter 126 or cannula. Advancement of the push wire 134 may cause a controlled eversion of the balloon 130, through the length of the body lumen (e.g., Fallopian tube).

According to some embodiments, a seal 137 may be disposed within the tube/catheter shaft 126 through which the push wire 134 passes as the push wire 134 actuates the balloon. In some embodiments, the seal 137 may be a conical seal disposed between a pressurized chamber 116 and the push wire 134. The conical seal 137 may allow the push wire 134 to advance through the catheter 126 to actuate the balloon 130 between an inverted position and an everted position while maintaining pressure in the catheter 126. Various embodiments of the present disclosure may provide an adjustable seal 135, disposed proximal to the conical seal 137. In response to a leak forming between the push wire 134 and the conical seal 137, the adjustable seal 135 may be adjusted to maintain the pressure required to move the balloon between the first inverted position and the second everted position. The adjustable seal 135 may be a rotating hemostasis valve, e.g., a device for maintaining seals between coaxial devices, and adjustable by a knob (not shown). In some embodiments, a hemostasis valve may be used as seal 135. The hemostasis valve may include a compressible gasket to provide a desired degree of sealing.

The knob 133 may be rotatably adjustable to adjust the seal 135. In use, a user may be able to adjust the knob 133 to tighten or loosen the knob 133. By tightening the knob 133, the seal 135 may be compressed, thereby collapsing around the push wire 134. The rotatable knob 133 may provide the user with improved control over the seal and the ability to react if there are any leaks from the conical seal 137.

As mentioned, a male luer lock fitting, or sheath knob, 164 including a Tuohy-Borst seal 136 connector may be included at the proximal end of the sheath 162. A Tuohy-Borst adapter that includes seal 136 is a medical device used for creating seals between devices and attaching catheters to other devices. The Touhy-Borst seal 136 may be tightened to have a slip fit with the catheter or cannula holding the sheath 162 in place. The sheath knob 164 may mate with a female luer lock fitting, if present, at an instrumentation port, on the working channel of the hysteroscope 20.

Figure 3:
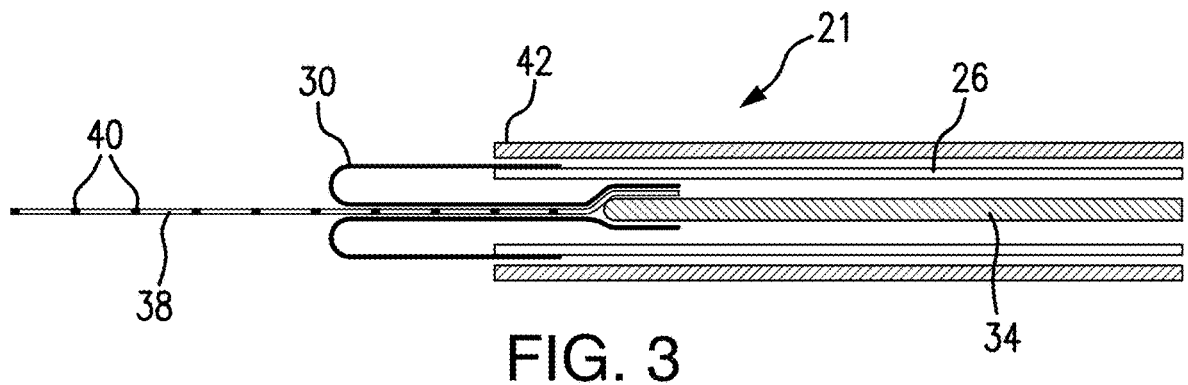
FIG. 3 illustrates a partial cross-sectional side view of an exemplary embodiment of an everting balloon catheter in a deployed state in accordance with the present disclosure.

As shown in FIG. 3, markers 40 may be disposed along the length of the suture 38. In some embodiments, the markers 40 may be approximately 1 mm long and may be disposed along the catheter on 5 mm increments. For example, FIG. 4 shows a plurality of markers 40 disposed along a longitudinal length of at least a portion of the sheath 42. The balloon 30 may be retractable into the sheath 42 to protect the collected cells when the device 20, 21, 23, 25 is removed from the patient. In some embodiments, markers 40 may be disposed on the sheath 42 and may indicate potential locations to separate the sample for analysis. Providing markers 40 on the outside of the catheter 20, 21, 23, 25 may allow a user to verify where the sample may be separated for analysis. Additionally or alternatively, one or more markers 40 may be placed on the balloon 30.

Referring now to FIGS. 5A and 5B, markers 40 may be disposed on the catheter 26. In some embodiments, and as illustrated in FIG. 5A, the balloon 30 may be deployable up to about 2 cm relative to the catheter 26. FIG. 5B shows the sheath 42 in an extended position relative to the balloon 30, which may protect the collected cells on the surface of the balloon 30 during removal from the patient. In some embodiments, the balloon 30 may be re-inverted into the catheter 26 after collection of cells. In some embodiments, the balloon 30 may remain everted and at least partially inflated, with the sheath 42 extending over it for protection during removal. In embodiments, after removal from the patient, the catheter 26 may be configured to be cut through at predetermined markers 40 along the catheter 26 as a guide. In this manner, a user may easily identify samples from a specific location in the body lumen (e.g. point "A" or "B").

According to exemplary embodiments of the present disclosure, a process for collecting and preparing cells from a body lumen (e.g., Fallopian tube) in a patient may include positioning a balloon (e.g., an inelastic balloon) in proximity with the Fallopian tube of the patient, and extending the balloon into the Fallopian tube. In some embodiments, the balloon may be extendable by eversion in a longitudinal direction into the Fallopian tube, such that the balloon does not substantially expand and dilate the lumen as the balloon everts or is extended into the body lumen (e.g., Fallopian tube). In some embodiments, the balloon may be extendable longitudinally into the body lumen, where a diameter of an inflated balloon may be up to approximately 10-15% greater than a diameter of a Fallopian tube. Radial expansion of the balloon may be limited or controlled up to a majority of the length of the balloon being substantially inelastic. It is appreciated that portions of a balloon that are not intended to be inserted within a lumen structure may be elastomeric and therefore may be expandable in diameter and compliant rather than substantially inelastic. Such a hybrid balloon may be suited in embodiments when a seal is desired with the UTJ. Exemplary of situations when a seal is desired may include irrigation of the lumen, filling the lumen with an imaging contrast, diagnosing obstructions, and/or topical contact with a therapeutic agent, such as a chemotherapeutic or an antibiotic agent.

The process may also include cell collection from the body lumen (e.g., Fallopian tube) on an outer surface of the balloon 30 by contacting a wall, or inner surface, of the Fallopian tube with the balloon 30, as well as on an extended portion from the balloon, such as a filament or suture, if present. It is understood that cell collection from the inner surface of the Fallopian tube may occur by contacting a balloon surface, filament, suture, or both. The balloon surface may include folds, overlaps, crinkles, or combinations thereof, although in some embodiments, the balloon surface may be substantially texture-free. In some embodiments, at least a partial rotation of the balloon 30 with respect to the catheter within the Fallopian tube, and/or an axial translation of the balloon within the lumen, may result in additional cell transfer to the balloon and/or the filament. Cell collection may also occur by the act of everting the balloon into the Fallopian tube at the beginning of the process, and/or retracting the balloon (e.g., into the sheath) at the end of the process. In some embodiments, the balloon may be formed of a material that may aid in cell collection during eversion, retraction, and/or rotational or axial translation.

Figure 7A:
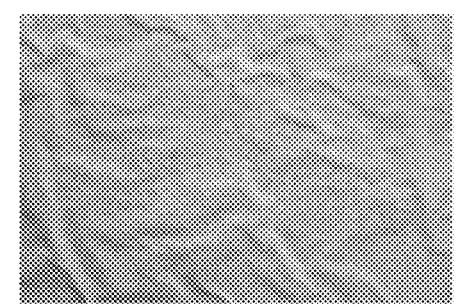
FIGS. 7A-7D illustrates exemplary embodiments of textures of an outer surface of a balloon in accordance with the present disclosure.
Figure 7B:
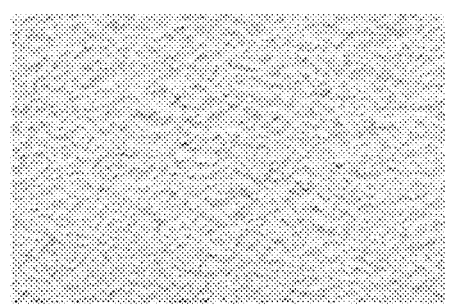
Figure 7C:
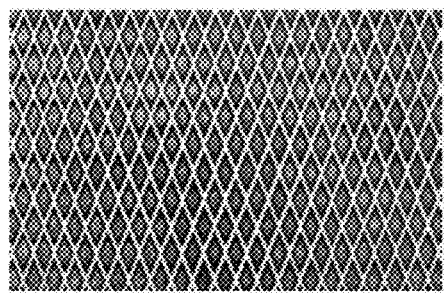
Figure 7D:
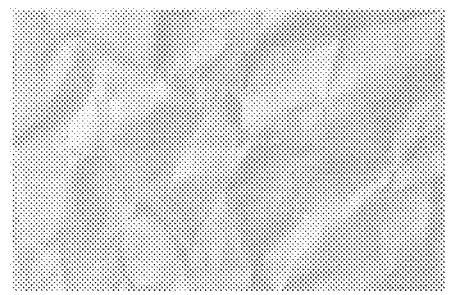

As described above, the outer surface of the balloon may have a textured surface, such as those shown in FIGS. 7A-7D, that may contact the wall, e.g., inner surface, of the body lumen (e.g., Fallopian tube). The textured surfaces 700, 705, 710, 715 may improve cell transfer to the balloon surface upon contact. For example, as shown in FIG. 7B, wrinkles, folds, and/or overlaps in the balloon surface may aid in cell collection. For example, the increased surface area of the balloon may aid in contact to the body lumen (e.g., Fallopian tube) for cell transfer. Additionally, in some embodiments, a textured balloon surface may also aid in retention of the collected cells on the outer surface of the balloon, as compared to a smoother balloon surface. For example, cells may be transferred to the balloon surface and captured within the wrinkles, folds, and/or overlaps, such that the cells may be retained until after removal of the device from the patient. It is understood that in some embodiments, the location of a given collected cell on the balloon surface may correlate with the original position of the cell in the body lumen. As a result, a review of cell pathology as a function of position on the balloon and/or suture may correlate with the region of the body lumen to aid in location of abnormalities therein. Positioning correlation may aid in targeting subsequent treatment procedures for the patient. In some embodiments, treatment may be more precisely delivered to a target area, which may reduce or limit potentially harmful exposure to healthy patient tissue. In some embodiments, a diagnosis and/or treatment may be determinable based on a location of the collected cells.

The process may further include removing the cells that have been collected from the inner surface of the body lumen and disposed on the outer surface of the balloon and/or the filament. In some embodiments, removing the cells from the patient may include withdrawing the balloon from the body lumen and from the patient. In some embodiments, cell collection may also include extending the sheath over the balloon, or re-inverting the balloon upon itself or into the catheter to protect the collected cells from contamination during removal from the patient, and may aid in retention of the cells on the balloon surface prior to withdrawing the balloon from the patient, thereby assuring that the cells harvested from the balloon surface are representative of the inner surface of the body lumen.

Figure 8:
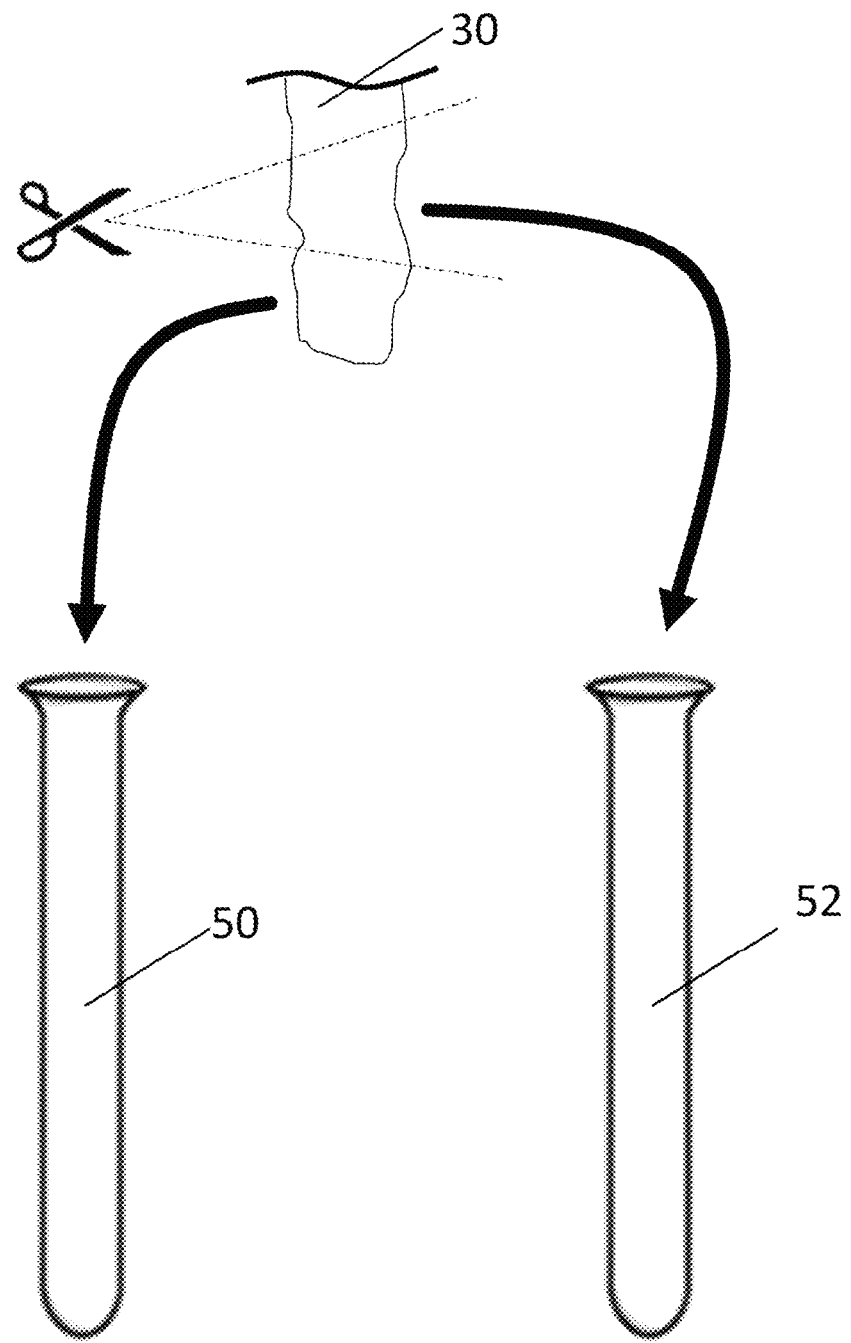
FIG. 8 illustrates an exemplary embodiment of collecting and preparing samples in accordance with the present disclosure.

When the device has been removed from the patient, any of the balloon, the filament, and/or the sheath may be cut to form a planar piece that is fixed and stained to cytology, or suspended in solution from which tissue cells are fixed and stained for cell evaluation, e.g., cancer screening. As shown in FIG. 8, at least one of the balloon or filament may be divided into at least two portions. In some embodiments, the sheath, which may cover the balloon after removal from the patient, may also be divided for sample analysis, although in other embodiments, the balloon may be exposed from the sheath for division without cutting the sheath. It is understood that the balloon and/or sheath may be divided transversely or longitudinally. In some embodiments, dividing the balloon, sheath, and/or filament may include separating the balloon, sheath, and/or filament, into at least a first portion and a second portion. In some embodiments, a first portion of the balloon, sheath, and/or filament may be separated, e.g., cut or severed, into a first receptacle (e.g., collection vial 50), and a second portion may be separated, e.g., cut or severed, into a second receptacle (e.g., collection vial 52). Although FIG. 8 illustrates receptacles as collection vials, it is understood that a receptacle may be any combination of a vial, container, beaker, repository, slide, dish, and/or the like. The balloon, sheath, and/or filament may be separated at additional points to produce additional portions. In some embodiments, the balloon, sheath, and/or filament may be separated at desired (e.g., predetermined) marker locations.

One of the receptacles may include sample preparation fluid for cytology while another receptacle may include a sample preservation liquid. Receptacles, (e.g., collection vials) for differing sample preparations and/or preservations may provide various methods of analysis for broader adoption, which may enable a greater number of medical professionals with expertise and/or equipment for patient care. It is understood that designations such as "first" and "second" portions may be used herein for clarity of understanding and not to limit the disclosure to a particular order or number of portions.

In some embodiments, the process may further include preparing a first cell sample from cells on at least one portion of the balloon for cytology. The first cell sample may be a slide for inspection under a microscope, which may be prepared by any number of common slide preparation techniques. Slide preparation may involve preparation of the slides followed by cell staining and visualization. The preparation of the slides may utilize cytoclips to hold the slide with a cytology funnel together, so that a cell suspension may be dropped into the funnel inclusive of cells floated free of the balloon surface. The slide-funnel complex may be set for centrifugation in a cytocentrifuge to concentrate and deposit cells from the funnel evenly onto the slide. However, some embodiments may provide a faster and easier method for preparing slides without the need for a cytoclip. The balloon, sheath, and/or filament may have a lower mass, and may be left in the collection vial in the centrifuge, which may allow the slides to be prepared without the need for a cytoclip. Accordingly, the processing of cell samples according to embodiments of the present disclosure may be expedited and may reduce or eliminate a possibility of contamination or operator error.

After centrifugation, the slides may be immersed in various staining and washing steps to prepare the slide for visualization. Some embodiments may include evaluating the first cell sample for malignancy or other abnormality.

Evaluation may occur manually, e.g., by a medical professional's evaluation of the cell sample. In some embodiments, an automated program may at least partially evaluate the cell sample. For example, a program may perform an initial evaluation of a patient's cell sample, and indicate one or more areas for further evaluation. A medical professional may receive a report, or other evaluation analysis, for further evaluation and, if necessary, treatment recommendations.

In some embodiments, cells may be retained from at least one portion of the balloon under conditions suitable for genetic testing and/or sequencing. Genetic testing and sequencing may be subsequently performed on the retained cells. From such genetic testing and/or sequencing the genetic code of the collected cells may be evaluated to provide a better understanding of the particular cancer or malignancy that is present in the collected cells. In some embodiments, a cell culture from a portion of the cells collected from a patient may be prepared. Using the prepared cell culture, further study and analysis may be conducted along with development and testing of medication and treatment for the particular cancer, abnormality, or malignancy, or combinations thereof, that is present in the collected cells.

Figure 9A:
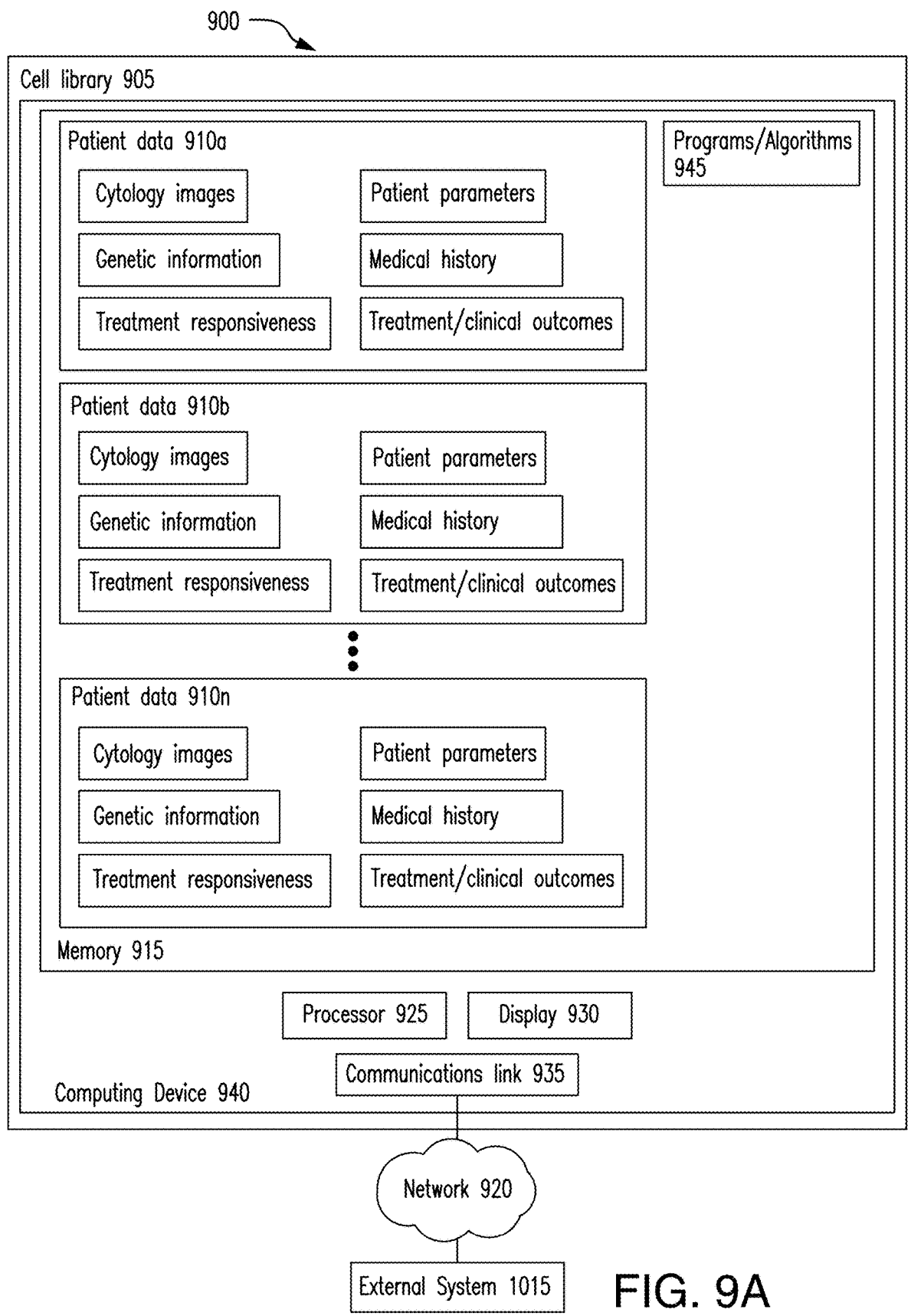
FIGS. 9A-9B are block diagrams illustrating exemplary embodiments of an operating environment in accordance with the present disclosure.
Figure 9B:
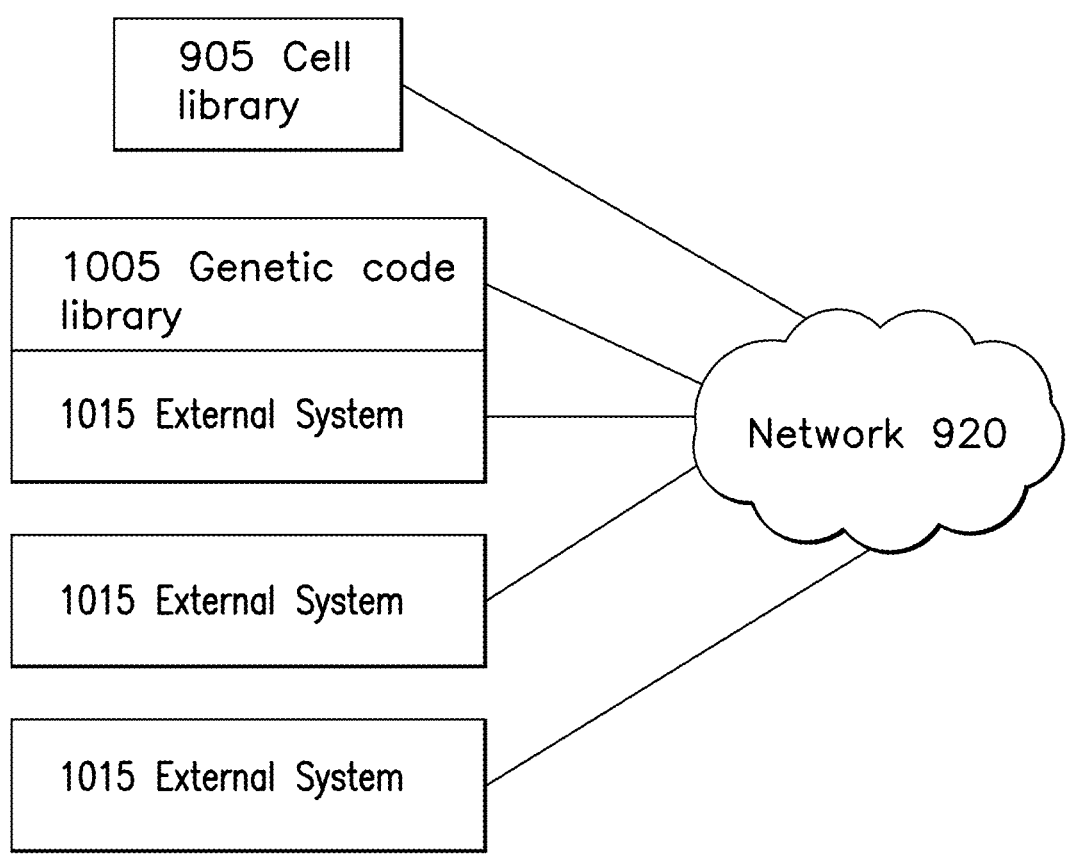

In some embodiments, for example with reference to FIGS. 9A, 9B, a cell collection and genetic analysis process may be carried out on a plurality of patients, generating patient data 910a, 910b, . . . 910n, where "n" is any number of patients. Patient data 910a, 910b, . . . 910n may include one or more of cytology images, genetic information about the cells collected, or treatment responsiveness, or combinations thereof. In some embodiments, additional patient parameters may be included in the data, such as patient age, sex, race, and sampled tissue location. As shown in schematic 900 in FIG. 9A, the patient data 910a, 910b, . . . 910n may be compilable into a cell library 905, i.e., a collection of patient tissue cells, a data library or both. In some embodiments, cells in the cell library may be subjected to genetic testing and sequencing to obtain the genetic code of the collected cells. The genetic code of the respective cells may also be recorded and compiled into a genetic code library. In some embodiments, the cell library and/or genetic code library may contain further information about the medical history of the patient from which each cell sample was collected, successful and unsuccessful treatment of the patient from which each cell sample was collected, and/or a clinical outcome of each patient from which each cell sample was collected. This information may be correlated with the collected cells from each patient. The cell samples and correlated information in the cell and/or genetic code library may be useful for analysis and study of diseases and cancers and aid with further understanding of causes and advances in treatments.

As shown in FIGS. 9A-9B, in some embodiments, the cell library 905 may be connected to network 920 through a communications link 935. Network 920 be in communication with and/or connectable to one or more external systems 1015, e.g., for receiving patient data 910a, 910b, . . . 910n, which may be stored in a memory 915 of the cell library 905.

The cell library 905 may include a computing device 940. Computing device 940 may include a processor 925, a memory 915, a communications link 935, and/or a display 930. The processor 925 may be communicatively coupled to memory 915, communications link 935, and/or display 930.

A processor 925 may include and/or may access various logic for performing processes according to some embodiments. The processor 925, or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

It is also understood that components of the processor 925 may be located within an accelerator, a processor core, an interface, an individual processor die, implemented entirely as a software application and/or the like.

Memory 920 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 430 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory 920 may store various information, e.g., patient data 910a, 910b, . . . 910n, as well as one or more programs, to perform various functions for analyzing cell cytology, e.g., such as identifying abnormalities and malignancies, and/or genomic information. In some embodiments, the memory 920 may include logic having application programming interfaces (APIs) and/or graphical user interfaces (GUIs) to read, write, and/or otherwise access information, such as via display 930, web interfaces, mobile application ("mobile applications," "mobile apps," or "apps"), and/or the like. In this manner, in some embodiments, an operator may search, visualize, read, add to, or otherwise access information associated the cell library 905. In some embodiments, memory unit 920 may receive and store patient data 910a, 910b, . . . 910n. In some embodiments, additional programs, algorithms, databases, or combinations thereof, e.g., identified as reference numeral 945, may also be stored in the memory 920 for cell analysis.

In some embodiments, an array of cells may be exposed to various therapeutic candidates such as organic molecules having a molecular weight of less than 2000 Daltons, antibodies, or small interfering RNAs, or combinations thereof, to assess effectiveness of potential candidates as therapeutics. In some embodiments, tissue cells from a new patient may be genotyped or phenotypically assessed by cytology image comparison to determine if the new subject cells match a library entry or represent a new type of pathology. A match of new patient cells with those in the library may rapidly inform treatment by identifying to a clinician successful or failed treatments performed on the library match patient, as well as suggested possible trial enrollment when no approved treatment exists.

A cell library may include physical cells stored under preservative conditions and/or electronic data relating to the collected luminal cells (e.g., cell library 905). Electronic copies of cells may also be stored in the cell library 905 with the genetic code of each cell and any additional information regarding patient history, treatment, and/or clinical outcome.

Compiling and maintaining a cell library of cells collected from a plurality of patients according to embodiments of the present disclosure may advantageously provide information about a patient. Some embodiments may include maintaining a cell library of cells collected from a plurality of patients according to various embodiments of the present disclosure and receiving a cell sample from a user. The received cell sample may be sent or transmitted to the cell library 905 from a physician, veterinarian, or other clinician, e.g., from an external system 1015. It is understood that external system 1015 is representative of any number of external systems that may be in communication with the cell library 905.

In some embodiments, the received sample may be collected and prepared by the user in accordance with the present disclosure, or by any other suitable processes for collecting and preparing such cells for analysis. In some embodiments, the preserved cells may be plated onto media and cultured in liquid media to generate additional cells to investigation. In some embodiments, genes from a given collected cell may be amplified by conventional techniques such a polymerase chain reaction (PCR) to create additional copies for investigation and the formation of test arrays.

In some embodiments, the process may include performing genetic testing and sequencing on the cell sample. The received cell sample may then be compared by the cell library. The comparison may include comparing the genetic code and/or the cells of the cell sample with the cell library 905 and/or genetic code library 1005. The comparison may identify similarities and differences between the received cell sample and the cells within the cell library. The comparison of the cell sample with the cells of the cell library may be accomplished manually or electronically via a database of the cells and/or genetic code of the cells in the cell library.

The process may further include reporting back to the clinician, researcher, or the patient from which the cell sample was collected regarding the cell sample. Such a reporting may include information regarding the similarities and/or dissimilarities of the cell sample with identified cells in the cell library. Additionally, such a reporting may include any additional information that has been correlated to cells within the library found to be similar to the received cell sample. For example, the reporting to the user or the patient may include information regarding successful and/or unsuccessful treatments used in the past on cells similar to the cell sample and clinical outcomes of such treatments. Such information may be a tool for diagnosis and/or prognosis of the patient. Additionally, the reporting may include diagnosis and prognostic information.

Any patents or publications mentioned in this specification are herein incorporated by reference to the same extent as if each individual publication was specifically and individually indicated to be incorporated by reference. The foregoing description is illustrative of particular embodiments of the disclosure, but is not meant to be a limitation upon the practice thereof.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Some embodiments of the disclosed systems may be implemented, for example, using a storage medium, a computer-readable medium or an article of manufacture which may store an instruction or a set of instructions that, if executed by a machine (i.e., processor or microcontroller), may cause the machine to perform methods and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method of collecting and preparing cells from a body lumen in a patient using a system that comprises a diagnostics device including a tube having a distal end and a proximal end, a metallic retraction marker disposed on the tube, a balloon having a first end coupled to the distal end of the tube, the balloon being disposed in the tube in a first, inverted position and movable to a second, everted position, and a sheath coaxial with the tube and slidably adjustable relative to the tube, wherein at least a portion of the sheath is optically transparent such that the retraction marker is visible to a user through the sheath, and wherein the retraction marker is positioned to allow the user to visualize and confirm that the balloon is protected by the sheath, the method comprising:
    everting the balloon into the body lumen;
    collecting the cells from the body lumen on an outer surface of the balloon when the balloon is everted;
    slidably adjusting the sheath relative to the tube such that the sheath covers at least a portion of the everted balloon and at least a portion of the cells collected on the outer surface of the balloon;
    using the retraction marker to visualize and confirm that the balloon is protected by the sheath;
    after visualizing and confirming that the balloon is protected by the sheath, removing the balloon including the cells collected on the outer surface of the balloon from the patient;
    separating at least a first portion of the balloon; and
    preparing a first cell sample from the cells on the first portion of the balloon.

2. The method according to claim 1, wherein the first portion of the balloon is separated into a first receptacle.

3. The method according to claim 2, wherein preparing the first cell sample from the cells on the first portion of the balloon comprises spinning the first receptacle in a centrifuge.

4. The method according to claim 1, wherein the body lumen is a Fallopian tube, and the balloon is inflated and extended longitudinally into the Fallopian tube during eversion.

5. The method according to claim 1, wherein the outer surface of the balloon is textured.

6. The method according to claim 1, further comprising separating at least a second portion of the balloon into a second receptacle and preparing a second cell sample from the cells on the second portion of the balloon.

7. The method of claim 1, wherein the diagnostics device further includes a filament extendable distally of the first end of the balloon, wherein the cells are collected on the filament, and wherein the method further comprises separating at least a portion of the filament into an additional receptacle and preparing an additional cell sample from the cells on the filament.

8. The method according to claim 1, further comprising evaluating the first cell sample for malignancies, or abnormalities, or both.

9. The method according to claim 1, further comprising retaining the first cell sample under conditions suitable for genetic testing of the cells.

10. The method according to claim 1, wherein the system further comprises a compiled cell library, and wherein the method further comprises performing a cytological analysis by analyzing the cells of the first cell sample against the compiled cell library.

11. The method according to claim 10, wherein the cell library includes information regarding treatments and clinical outcomes of patients correlated with cells of the compiled cell library.

12. A method of collecting and preparing cells from a body lumen in a patient using a system that comprises a diagnostics device including a tube having a distal end and a proximal end, a tubular metal retraction marker disposed on and around the tube, a balloon having a first end coupled to the distal end of the tube, the balloon being disposed in the tube in a first, inverted position and movable to a second, everted position, and a sheath coaxial with the tube and slidably adjustable relative to the tube, wherein at least a portion of the sheath is optically transparent such that the retraction marker is visible to a user through the sheath, the method comprising:
    everting the balloon into the body lumen;
    collecting the cells from the body lumen on an outer surface of the balloon when the balloon is everted;
    slidably adjusting the sheath relative to the tube such that the sheath covers at least a portion of the everted balloon and at least a portion of the cells collected on the outer surface of the balloon, wherein the retraction marker is used to visualize and confirm that the balloon is protected by the sheath;
    after visualizing and confirming that the balloon is protected by the sheath, removing the balloon including the cells collected on the outer surface of the balloon from the patient;
    separating at least a first portion of the balloon; and
    preparing a first cell sample from the cells on the first portion of the balloon.

13. The method according to claim 12, wherein the first portion of the balloon is separated into a first receptacle.

14. The method according to claim 13, wherein preparing the first cell sample from the cells on the first portion of the balloon comprises spinning the first receptacle in a centrifuge.

15. The method according to claim 12, wherein the body lumen is a Fallopian tube, and wherein the balloon is inflated and extended longitudinally into the Fallopian tube during eversion.

16. The method according to claim 12, wherein the outer surface of the balloon is textured.

17. The method according to claim 12, further comprising evaluating the first cell sample for malignancies, or abnormalities, or both.

18. The method according to claim 12, further comprising retaining the first cell sample under conditions suitable for genetic testing of the cells.

19. The method according to claim 12, wherein the system further comprises a compiled cell library, wherein the method further comprises performing a cytological analysis by analyzing the cells of the first cell sample against the compiled cell library.

20. The method according to claim 19, wherein the cell library includes information regarding treatments and clinical outcomes of patients correlated with cells of the compiled cell library.

* * * * *